US011185224B2

(12) United States Patent
AlRegib et al.

(10) Patent No.: US 11,185,224 B2
(45) Date of Patent: Nov. 30, 2021

(54) OCULAR MONITORING HEADSET

(71) Applicants: Georgia Tech Research Corporation, Atlanta, GA (US); Emory University, Atlanta, GA (US)

(72) Inventors: Ghassan AlRegib, Atlanta, GA (US); Yousuf M. Khalifa, Atlanta, GA (US); Melvin J. Mathew, Atlanta, GA (US); Dogancan Temel, Atlanta, GA (US)

(73) Assignees: Emory University, Atlanta, GA (US); Georgia Tech Research Corporation, Atlanta, GA (US)

(*) Notice: Subject to any disclaimer, the term of this patent is extended or adjusted under 35 U.S.C. 154(b) by 308 days.

(21) Appl. No.: 16/352,363

(22) Filed: Mar. 13, 2019

(65) Prior Publication Data
US 2019/0282087 A1    Sep. 19, 2019

Related U.S. Application Data

(60) Provisional application No. 62/642,279, filed on Mar. 13, 2018.

(51) Int. Cl.
*A61B 3/113* (2006.01)
*A61B 3/14* (2006.01)
*H04N 5/225* (2006.01)
*A61B 3/00* (2006.01)

(52) U.S. Cl.
CPC ............ *A61B 3/113* (2013.01); *A61B 3/0008* (2013.01); *A61B 3/14* (2013.01); *H04N 5/2253* (2013.01); *H04N 5/2254* (2013.01)

(58) Field of Classification Search
CPC ......... A61B 3/113; A61B 3/0008; A61B 3/14; H04N 5/2253; H04N 5/2254
USPC .......................................... 351/205-206, 246
See application file for complete search history.

(56) References Cited

U.S. PATENT DOCUMENTS

| 7,347,553 | B2* | 3/2008 | Matsumoto | A61B 3/14 351/205 |
| 7,677,730 | B2* | 3/2010 | Shimizu | A61B 3/14 351/206 |
| 8,292,433 | B2* | 10/2012 | Vertegaal | H04N 7/18 351/209 |
| 2007/0236663 | A1* | 10/2007 | Waldorf | A61B 3/112 351/206 |
| 2011/0237999 | A1* | 9/2011 | Muller | A61B 3/107 604/20 |

(Continued)

Primary Examiner — James R Greece
(74) Attorney, Agent, or Firm — Troutman Pepper Hamilton Sanders LLP; Ryan A. Schneider

(57) ABSTRACT

A system for monitoring ocular movement can comprise a housing, a plurality of light sources, at least one imager, and a controller. The housing can define a cavity configured to allow each eye of a patient to view an interior region of the housing. The plurality of light sources can be oriented within the interior region of the housing. The at least one imager can be oriented to capture an image of an eye of a patient during an evaluation. The at least one controller can comprise at least one processor and a non-transitory computer readable medium storing instructions. The instructions can be executed by the processor and cause the controller to receive image data from the at least one imager and illuminate the plurality of light sources in a predetermined and reconfigurable sequence.

21 Claims, 15 Drawing Sheets

(56) References Cited

U.S. PATENT DOCUMENTS

2013/0308099 A1* 11/2013 Stack ................ A61B 5/163
　　　　　　　　　　　　　　　　　　351/209
2014/0160434 A1* 6/2014 Brown, Jr. .......... A61B 3/0025
　　　　　　　　　　　　　　　　　　351/210

* cited by examiner

FIG. 11

OCULAR MONITORING HEADSET

CROSS-REFERENCE TO RELATED APPLICATIONS

This application claims priority to U.S. Provisional Patent Application No. 62/642,279, filed 13 Mar. 2018, which is hereby incorporated by reference herein in its entirety as if fully set forth below.

FIELD OF THE DISCLOSURE

The present disclosure relates to systems and methods for monitoring ocular responses, and more particularly systems and methods for capturing images of a patient's eyes, analyzing the images, and evaluating ocular responses to various stimuli.

BACKGROUND

There are systems and methods for evaluating ocular response. Further, there are a plurality of tests and analyses that can be performed and evaluated for various eye conditions. Each of these evaluations may require different medical devices and associated analysis techniques to make a proper evaluation for diagnosis or subsequent treatment. For example, a general eye exam may require an eight-point analysis comprising: visual acuity, pupil analysis, extraocular motility and alignment, intraocular pressure, confrontational visual fields, an external examination, a slit-lamp examination or fundoscopic examination. Other tests can include an ocular biometry, keratometry analysis or an Optical Coherence Tomography (OCT) analysis. Each of these tests can require a doctor or other examiner to use a separate device to complete the evaluation. Thus, a full eye exam can be a tedious process. Further, the accessibility of these tests to senior citizens or persons in underserved communities or in other countries with decreased ability to receive adequate eyecare increases the difficulty of completing these evaluations. Thus, there is a need for improved systems and methods for completing the plurality of tests efficiently, while being able to analyze, transmit and provide therapy with similar efficacy.

SUMMARY

Embodiments of the present disclosure address these concerns as well as other needs that will become apparent upon reading the description below in conjunction with the drawings. Briefly described, embodiments of the present disclosure relate generally to systems and methods for monitoring ocular activity. An embodiment provides a system for monitoring ocular movement. The system can comprise a housing, a plurality of light sources, at least one imager, and at least one controller. The housing can define a cavity. The cavity can be configured to allow each eye of a patient to view an interior region of the housing. The plurality of light sources can be oriented within the interior region of the housing. The at least one imager can be oriented to capture an image of an eye of a patient during an evaluation. The at least one controller can comprise at least one processor and a non-transitory computer readable medium to store instructions. The instructions, when executed by the at least one processor, can cause the controller to receive image data from the at least one imager and to illuminate the plurality of light sources in a predetermined and reconfigurable sequence.

In any of the embodiments described herein, the housing can be configured to separate the cavity into a distinct region for each eye such that light emanating from a first light source of the plurality of light sources is confined to the distinct region.

In any of the embodiments described herein, the plurality of light sources can comprise a plurality of light emitting diodes (LEDs). The plurality of LEDs can be separated into distinct groups wherein each distinct group is separately controllable by the at least one processor.

In any of the embodiments described herein, the at least one imager can be coupled to a gimbal system. The gimbal system can be configured to adjust a focus region by the at least one imager upon an eye of a patient.

In any of the embodiments described herein, the system can further comprise an aperture device configured to transmit a collimated beam of light towards one or more regions of an eye of a patient.

In any of the embodiments described herein, the aperture device can be oriented in a fixed position within the interior region of the housing.

In any of the embodiments described herein, the system can further comprise a sprayer configured to spray one or more of a particulate, a liquid, or air towards an eye of a patient.

In any of the embodiments described herein, the system can further comprise a lens coupled to the housing and configured to orient a focal region of the lens onto a section of an interior portion of an eye of a patient beneath a surface of the eye.

In any of the embodiments described herein, the instructions, when executed by the processor, can cause the controller to illuminate a first light source in the plurality of light sources at a first time; receive first image data from the imager indicative of a first image of a left eye of a patient during illumination of the first light source; illuminate a second light source in the plurality of light sources at a second time different than the first time; and receive second image data from the imager indicative of a second image of a left eye of a patient during illumination of the second light source.

In any of the embodiments described herein, the instructions, when executed by the processor, can further cause the controller to illuminate a third light source in the plurality of light sources at a third time different from the first and second times; receive third image data from the imager indicative of a third image of a right eye of a patient during illumination of the third light source; illuminate a fourth light source in the plurality of light sources at a fourth time different than the first, second, and third times; and receive fourth image data from the imager indicative of a fourth image of a right eye of a patient during illumination of the fourth light source.

In another embodiment, a method for monitoring ocular movement can comprise providing an ocular monitoring system. The ocular monitoring system can comprise a housing, at least one imager, and a plurality of light sources. The housing can define a cavity. The cavity can be configured to allow each eye of a patient to view an interior region of the housing. The plurality of light sources can be oriented within the interior region of the housing. The at least one imager can be oriented to capture an image of an eye of a patient during an evaluation. The method can further comprise illuminating the plurality of light sources at a predetermined sequence and capturing images of at least one eye of a patient in response to the illuminating the plurality of light sources at the predetermined sequence.

In any of the embodiments described herein, illuminating the plurality of light sources at the predetermined sequence can comprise illuminating a first light source in the plurality of light sources at a first time and illuminating a second light source in the plurality of light sources at a second time different than the first time. Capturing images of at least one eye of a patient can comprise capturing a first image of a left eye of a patient during illumination of the first light source and capturing a second image of a left eye of a patient during illumination of the second light source.

In any of the embodiments described herein, illuminating the plurality of light sources at the predetermined sequence can further comprise illuminating a third light source in the plurality of light sources at a third time different than the first and second times and illuminating a fourth light source in the plurality of light sources at a fourth time different than the first, second, and third times. Capturing images of at least one eye of a patient can comprise capturing a third image of a right eye of a patient during illumination of the third light source and capturing a fourth image of a right eye of a patient during illumination of the fourth light source.

In any of the embodiments described herein, the monitoring system can further comprise a collimated light source located within the interior region of the housing. The method can further comprise: illuminating a first region of an eye of a patient with a collimated beam of light; capturing an image of the first region of the eye of the patient; illuminating a second region of an eye of a patient with the collimated beam of light; and capturing an image of the second region of the eye of the patient.

In any of the embodiments described herein, the collimated light source can be oriented in a fixed position within the interior region of the housing.

In any of the embodiments described herein, the method can further comprise spraying, using a sprayer, at least one of a fluid, air, or a particulate towards an eye of a patient and capturing an image of an eye of the patient in response to the spraying.

In any of the embodiments described herein, the method can further comprise: inserting a lens to a position between the imager and eye of a patient; focusing the imager on a portion of an eye of the patient beneath the surface of the eye; and capturing an image of the portion of an eye of the patient.

Another embodiment provides a system for monitoring ocular movement. The system can comprise a housing, a first plurality of light sources, a first imager, a first collimated light source, a first focusing lens, and a controller. The housing can define a cavity. The first plurality of light sources can be oriented within a first distinct interior region of the housing. The first imager can be oriented within the first distinct interior region and configured to capture an image of a first eye of a user of the system. The first collimated light source can be oriented in the first distinct interior region and configured to direct the first collimated beam of light towards a first region of the first eye of the user. The first focusing lens can be configured to focus the first imager on an interior region of the first eye of the user beneath a surface of the first eye of the user. The controller can be configured to: illuminate a first light source in the first plurality of light sources at a first time; capture an image of the first eye of the user during illumination of the first light source; illuminate a second light source in the first plurality of light sources at a second time different than the first time; cause the first imager to capture an image of the first eye of the user during illumination of the second light source; cause the first imager to capture an image of the region of the first eye of the user illuminated by the first collimated light source; and capture an image of the interior region of the first eye of the user beneath the surface of the eye of the user.

In any of the embodiments described herein, the system can further comprise a second plurality of light sources, a second imager, a second collimated light source, and a second focusing lens. The second plurality of light sources can be oriented within a second distinct interior region of the housing. The second imager can be oriented within the second distinct interior region and configured to capture an image of a second eye of a user of the system. The second collimated light source can be oriented in the second distinct interior region and configured to direct a second collimated beam of light towards a region of the second eye of the user. The second focusing lens can be configured to focus the second imager on an interior region of the second eye of the user beneath a surface of the second eye of the user. The controller can be further configured to: illuminate a first light source in the second plurality of light sources at a third time different from the first and second times; cause the second imager to capture an image of the second eye of the user during illumination of the first light source in the second plurality of light sources; illuminate a second light source in the second plurality of light sources at a fourth time different than the first, second, and third times; cause the second imager to capture an image of the second eye of the user during illumination of the second light source in the second plurality of light sources; cause the second imager to capture an image of the region of the second eye of the user illuminated by the second collimated light source; and capture an image of the interior region of the second eye of the user beneath the surface of the second eye of the user.

In any of the embodiments described herein, the first focusing lens can be movable between a storage position and a focusing position.

These and other aspects of the present disclosure are described in the Detailed Description below and the accompanying figures. Other aspects and features of embodiments of the present disclosure will become apparent to those of ordinary skill in the art upon reviewing the following description of specific, example embodiments of the present disclosure in concert with the figures. While features of the present disclosure may be discussed relative to certain embodiments and figures, all embodiments of the present disclosure can include one or more of the features discussed herein. Further, while one or more embodiments may be discussed as having certain advantageous features, one or more of such features may also be used with the various embodiments of the disclosure discussed herein. In similar fashion, while example embodiments may be discussed below as device, system, or method embodiments, it is to be understood that such example embodiments can be implemented in various devices, systems, and methods of the present disclosure.

BRIEF DESCRIPTION OF THE DRAWINGS

Various embodiments of the present disclosure together with further objects and advantages may be best understood by reference to the following description taken in conjunction with the accompanying drawings, and several figures, which are not necessarily drawn to scale, and in which like reference numerals identify like elements.

FIG. 11 depicts an example display on a graphical user interface for the control of the illumination sequence in an ocular monitoring system, in accordance with an exemplary embodiment.

DETAILED DESCRIPTION OF EMBODIMENTS

Figure 1:
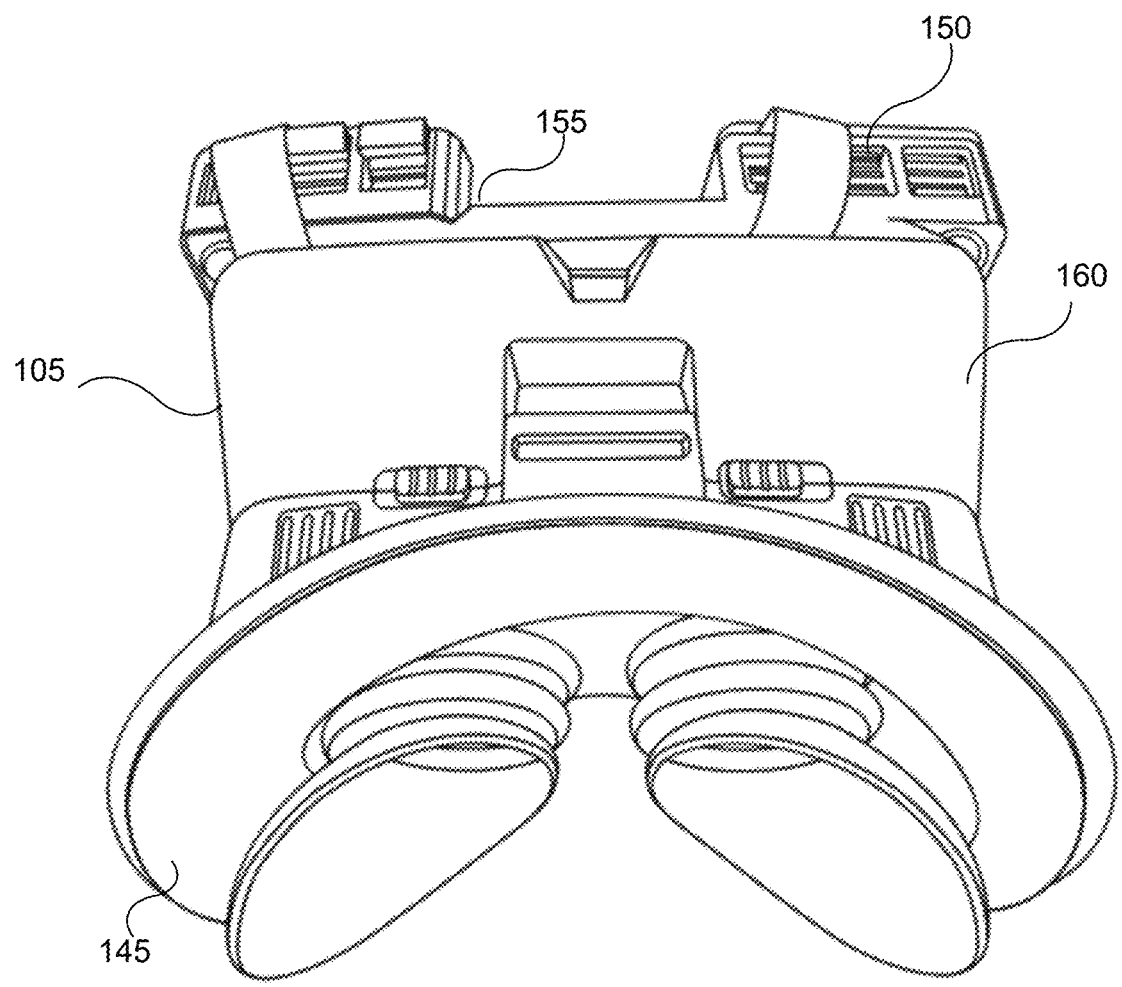
FIG. 1 depicts an isometric view of an ocular monitoring system, in accordance with an exemplary embodiment.

Illustrative embodiments of the disclosure will now be described more fully hereinafter with reference to the accompanying drawings, in which some, but not all embodiments of the disclosure are shown. The disclosure may be embodied in many different forms and should not be construed as limited to the embodiments set forth herein; rather, these embodiments are provided so that this disclosure will satisfy applicable legal requirements.

Whenever appropriate, terms used in the singular also will include the plural and vice versa. The use of "a" herein means "one or more" unless stated otherwise or where the use of "one or more" is clearly inappropriate. The use of "or" means "and/or" unless stated otherwise. The use of "comprise," "comprises," "comprising," "include," "includes," and "including" are interchangeable and not intended to be limiting. The term "such as" also is not intended to be limiting. For example, the term "including" shall mean "including, but not limited to."

The following description is provided as an enabling teaching of the disclosed articles, systems, and methods in their best, currently known embodiments. To this end, those skilled in the relevant art will recognize and appreciate that many changes can be made to the various aspects of the articles, systems, and methods described herein, while still obtaining the beneficial results of the disclosure. It will also be apparent that some of the desired benefits of the present disclosure can be obtained by selecting some of the features of the present disclosure without utilizing other features. Accordingly, those who work in the art will recognize that many modifications and adaptations to the present disclosure are possible and can even be desirable in certain circumstances and are a part of the present disclosure. Thus, the following description is provided as illustrative of the principles of the present disclosure and not in limitation thereof.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

As used herein, the terms "optional" or "optionally" mean that the subsequently described event or circumstance may or may not occur, and that the description includes instances where said event or circumstance occurs and instances where it does not.

The word "or" as used herein means any one member of a particular list and also includes any combination of members of that list.

As used throughout, the singular forms "a," "an" and "the" include plural referents unless the context clearly dictates otherwise. Thus, for example, reference to "a gasket" can include two or more such gaskets unless the context indicates otherwise.

Figure 2:
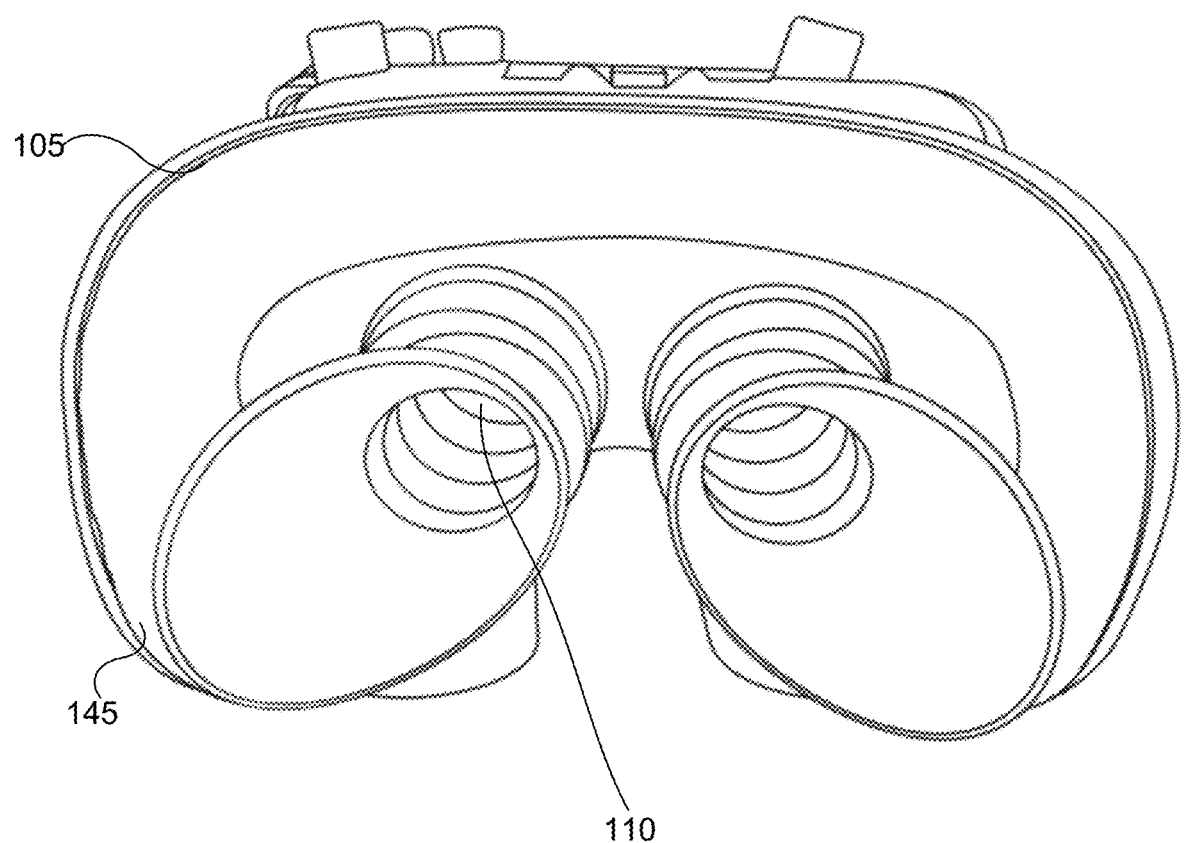
FIG. 2 depicts a front view of the ocular monitoring system depicted in FIG. 1
Figure 3:
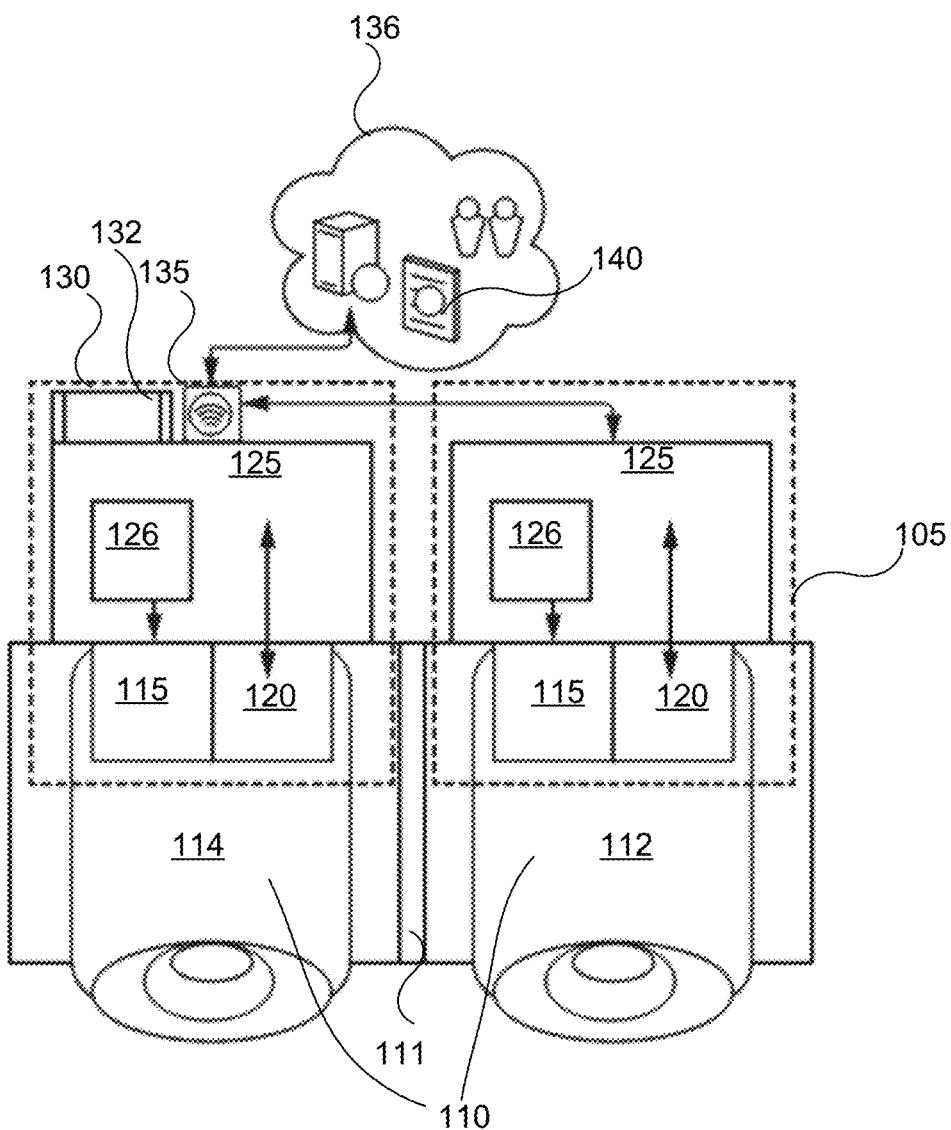
FIG. 3 depicts a schematic of the ocular monitoring system in FIG. 1

As shown in FIGS. 1-3, the eye monitoring system 100 can comprise a plurality of components. For example, the system 100 can comprise a housing 105 wherein the housing defines a cavity 110. The cavity 110 can be subdivided into two regions, a right cavity 112 and a left cavity 114. In a further aspect, a light source 115 can be oriented within the cavity 110. The system 100 can also comprise at least one imager 120 oriented in proximity to the light source 115 and disposed within the cavity 110. The light source 115 can be illuminated in response to a lighting sequence executed by a controller 125. The instructions for operating the controller 125 as well as storing images taken by the imager 120 can be done by the storage medium 130. The system can also comprise a communications module 132 configured to facilitate data communication external to the housing 105.

Housing 105 can be a structure configured to interface with the orbital region of a patient's eyes. In a further aspect of the embodiment, the housing can comprise padding 145 to support an interface between a patient's orbital region and the housing 105. The housing 105 can define a cavity 110 such that the patient can view into the interior of the housing 105. In a further aspect, the housing 105 can separate the cavity 110 into two distinct regions (one region for each eye), a right cavity 112 and a left cavity 114. The separation can be completed by a splitter 111 oriented substantially in the cavity 110 such that the right cavity 112 and the left cavity 114 have substantially the same volume. The splitter 111 can be configured to be a permanent fixture in the cavity. In another embodiment, the splitter 111 can be a removable fixture in the cavity.

In one aspect, the housing 105 can be configured to be portable. In a portable configuration, the housing 105 can be affixed to the patient's head using a harness (not shown). In another aspect, the housing 105 can be stabilized in a non-portable configuration. In the non-portable configuration, the housing 105 can be affixed to a fixed surface or movable base using a control arm (not shown). For example, one end of the control arm can be coupled to a wall, floor or movable base; the other end of the arm can be coupled to the housing 105. In a further aspect, the control arm can be controllable by the controller 125 such that the housing 105 in free space can be manipulated. For example, plurality of controllable servo motors can be attached to the arm. Further, the controller 125 can send instructions to the servomotor to orient the housing 105 in frees pace. In this embodiment, the harness can be configured to ensure that the patient's eyes maintain an interface with the housing 105.

Figure 4B:
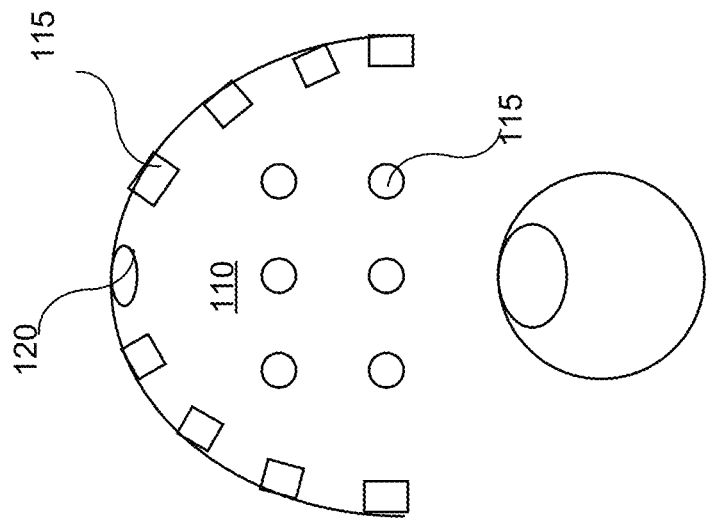
FIGS. 4 A-B depict schematic top cross-sectional views of an array of light sources within a cavity of an ocular monitoring system, in accordance with an exemplary embodiment.
Figure 4A:
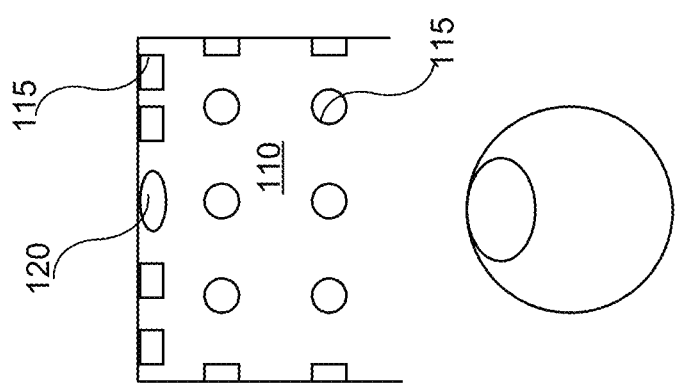

The light source 115 can be displaced in the cavity 110. As shown in FIG. 4A-4B, the light source 115 can comprise a plurality of sources dispersed within the cavity 110. To capture additional types of images, the light source can comprise different types of light. For example, the light source 115 can comprise visible light, infrared light, black light, monochromatic light, or laser. Additional types of light are possible. In other aspects, the light source 115 can provide sufficient illumination to support capturing an image in the absence of light, such as night-vision lighting. In yet another aspect, the light source 115 can comprise light emitting diodes LEDs. In a further aspect, the arrangement of light sources can comprise a screen of light emitting diodes, wherein the screen can be affixed the internal walls defining the cavity 110. In another embodiment, the screen of the light source 115 can be curved. In yet another aspect, the light sources 115 can be individually controlled by an illumination sequence executed by the controller 125. Similarly, the light sources 115 can also be configured to be illuminated in select groupings.

Figure 5A:
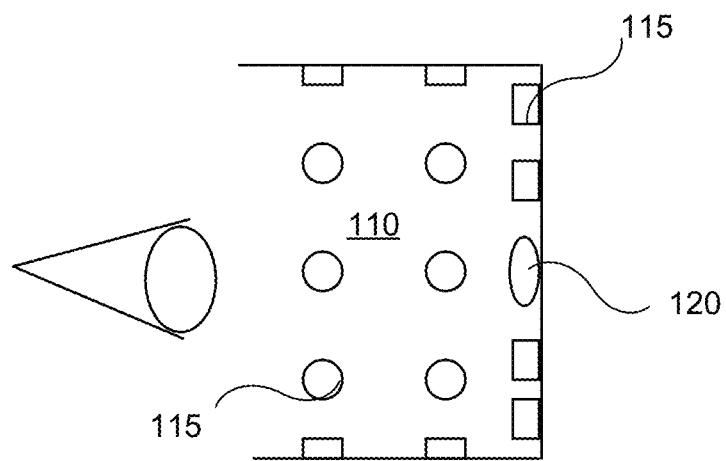
FIGS. 5A-B depict schematic side cross-sectional views of an array of light sources of an ocular monitoring system, in accordance with an exemplary embodiment.
Figure 5B:
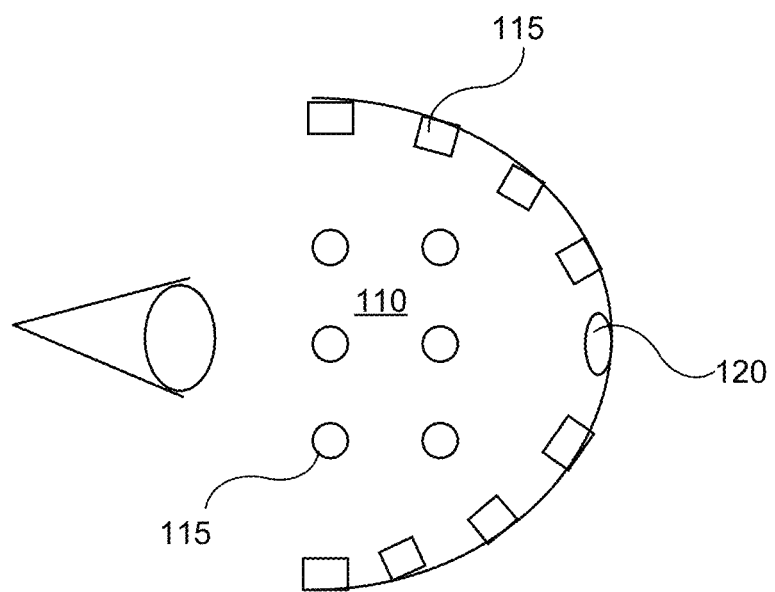

As shown in FIG. 5A-5B, the light sources 115 can be dispersed throughout the respective cavities 112, 114. In the absence of the splitter 111, the same light source 115 can be seen by both eyes simultaneously. When the splitter 111 is used to create two distinct cavities 112, 114, each cavity can be illuminated by one or more respective light sources 115 only viewable in that respective cavity. In a further aspect, the arrangement of the light can be configured in a three-dimensional orientation. The arrangement of the light sources 115 can be oriented based on calculations to simulate varying depths within the cavity. For example, the illumination sequence can include variations in brightness in addition to timing to simulate variable distances within the cavity. In a further aspect, the light source 115 can also be configured to display letters, symbols, or a combination thereof.

Figure 6:
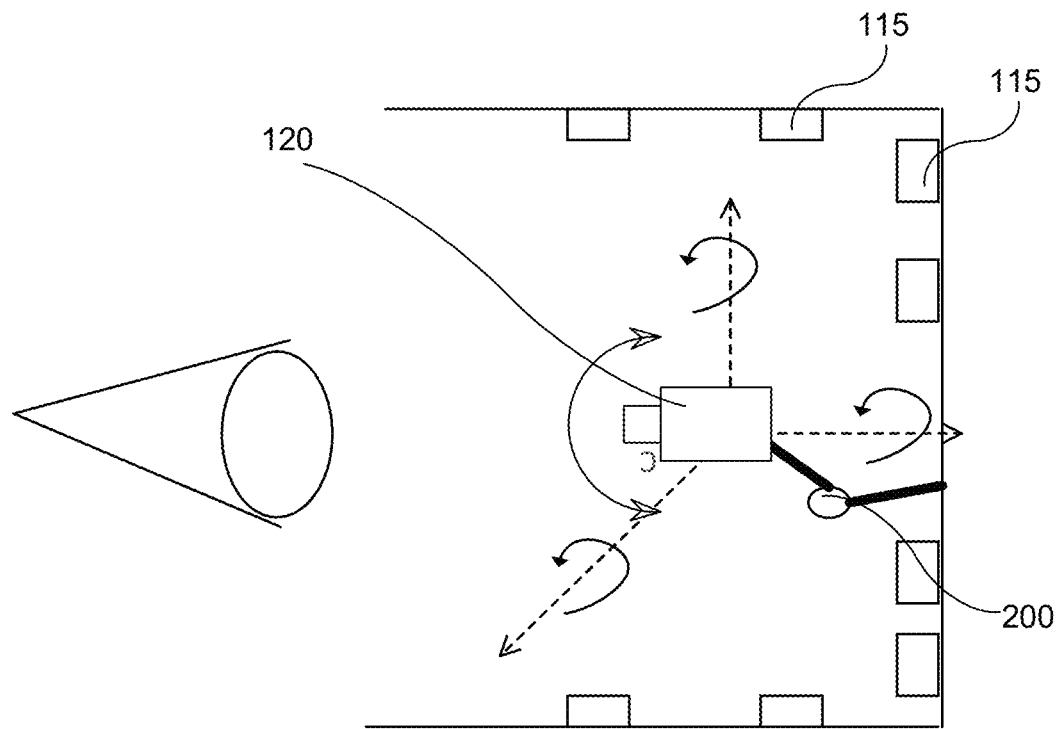
FIG. 6 depicts a schematic side cross-sectional of the cavity depicting an imager with a gimbal, in accordance with an exemplary embodiment.

The housing 105 can also comprise at least one imager 120 for each cavity. Within a respective cavity 112 or 114, the imager 112 is oriented to take images of the eye during an illumination sequence or other test. As shown in FIG. 6 the imager 120 can be oriented on a gimbal 200. In a further aspect, the gimbal structure 200 can also be controllable by the controller 125 to adjust the location of the imager 120 within the cavity 110. The imager 120 can be moved along the walls of the cavity 110 to adjust the angle and distance of an image captured by the imager 120 without requiring movement of the patient's eye. In an aspect, the gimbal can allow the imager to have increased range of motion along the X-Y plane within the cavity. Similarly, the gimbal can increase the range of motion in the X-Z plane and Y-Z plane. Further the gimbal can allow rotation around X, Y and Z axes oriented in the cavity. In yet another aspect the imager gimbal 200 can be motorized and controllable by the controller 125. In a further aspect, the illumination sequences for the light sources 115 can be coordinated with the controllable motion of the imager 120 with the gimbal 200 to increase the type of images acquired.

In other aspects, the imager 120 can be a visible light camera, such as an RGB camera, that captures luminance and chrominance components. In yet another aspect, the imager 120 can be an apparatus that captures the infrared light. The imager can be a night vision camera. In a further aspect, the imager 120 can be an apparatus that captures the heat spectrum and the thermal radiation of the imaged objects. In another embodiment, the imager 120 can be an apparatus that captures depth field and the entire light field in a three-dimensional fashion. In yet another aspect, the imager 120 can be an apparatus that capture the motion field. In further another aspect, the imager 120 can be an apparatus that captures light and distance range. In further yet another aspect, imager 120 can be an apparatus that detects and images microscopic structures. In yet another aspect, imager 120 can be a microscopic sensor.

In yet another aspect, a plurality of imagers can be dispersed in the cavity. The plurality of imagers can be displaced at various locations and angles in the cavity 110 to provide a greater variety of images. The controller 125 can be further configured to use the plurality of images from the plurality of imagers to generate various views such as three-dimensional views of the eye. Further, all of these images can be processed by the controller 125 and stored on a non-transitory medium 130. In other aspects, the images can be transmitted to an external storage device, such as a $3^{rd}$ party storage database or the external storage system 136 for manipulation by the GUI 140. In yet another aspect, the GUI 140 can be coupled to an exterior portion of the housing 105.

The communication module 132 can facilitate data transfer between the housing 105 and an external system 136. In one aspect, the data transfer can be facilitated by the antennae 135. In a further aspect, the communications module 132 can be used to receive illumination sequences or imager orientation instructions from an external source, these instructions can then be sent to controller 125 for execution. The communication module 132 can further comprise a speaker and a microphone to facilitate two-way communication with a patient that is interfacing with the system 100. In addition, the microphone feature can be used by the patient to provide feedback to a potential health care provider. In a further aspect, the communication module 132 can facilitate communication between a patient and healthcare provider when the two are in different locations. The communication module 132 can interface with any type of computer networking arrangement used to exchange data in a localized area, such as WIFI, Bluetooth™ Ethernet, and other suitable network connections that enable components of system 100 to interact with other systems. The communications module 132 can also facilitate communication with external networks such as internet, a private data network or virtual private network using a public network.

As discussed, the controller 125 can be configured to control a plurality of components for the system 100. In an aspect, the controller 125 can receive instructions from a storage medium 130 to execute potential lighting sequences for the lighting sources 115. In a further aspect, the system can comprise a plurality of controllers wherein each controller can be tasked with a particular task for operating the system. For example, the controller 125 can comprise one or more of a microprocessor, microcontroller, digital signal processor, co-processor or the like or combinations thereof. Controller 125 can constitute a single core or multiple core processor that executes parallel processes simultaneously. For example, controller 125 can be a single core controller that is configured with virtual processing technologies. In certain embodiments, controller 125 can use logical processors to simultaneously execute and control multiple processes. Controller 125 can implement virtual machine technologies, or other similar known technologies to provide the ability to execute, control, run, manipulate, store, etc. multiple software processes, applications, programs, etc. For example, controller 125 can also comprise an LED controller 126 for executing LED illumination sequences. The one or more processors of the controller 125 can host a set of instructions that analyze acquired images from the imager 125 and stores the analysis results in the memory 130 or use the results to create new instructions to the controller 125. One of ordinary skill in the art would understand that other types of processor arrangements could be implemented that provide for the capabilities disclosed herein.

The memory 130 can comprise implementations, one or more suitable types of memory (e.g. such as volatile or non-volatile memory, random access memory (RAM), read only memory (ROM), programmable read-only memory (PROM), erasable programmable read-only memory (EPROM), electrically erasable programmable read-only memory (EEPROM), magnetic disks, optical disks, floppy disks, hard disks, removable cartridges, flash memory, a redundant array of independent disks (RAID), and the like), for storing files including an operating system, application programs (including, for example, a web browser application, a widget or gadget engine, and or other applications, as necessary), executable instructions and data.

In a further aspect, controller 125, imager 120 and memory 130 can used to capture images for subsequent identification. Captured images of one or more of the eyes can be analyzed to identify the individual. One or more parts of the eye can be imaged for identification, including, but not limited to: the iris, retina, pupil, pupil movement, pupil reflex, eye outer structure, anterior segments, eyelid color, saccade among many other features of one or more of the eyes. The imager 120 can be any apparatus that captures different bands of the light field. Captured images by an imager 120 can be analyzed to identify the individual based on one or more factors including but not limited to color, motion, dryness, history, reflexes, intensity, gaze, synchronization between the two eyes, thermal distribution, microscopic structures, or any such factors. Further, the identification mechanism can be used to track the history of the eye conditions and, subsequently, enable progression tracking of one or more medical condition and medication compliance. In another aspect, the identification mechanism can be used as a login mechanism to access certain functionalities and personalized features in the device.

The system 100 can further comprise interface ports 150. In an aspect, the interface ports 150 can be configured to output or receive data. For example, the interface port 150 can be a USB drive allowing for the direct connection to a printer. The interface ports 150 can comprise hardware, firmware and/or software that enables communication with various peripheral devices, such as media drives (e.g., magnetic disk, solid state, or optical disk drives), other processing devices. In some embodiments, the interface ports can include a serial port, a parallel port, a general-purpose input and output (GPIO) port, a game port, a universal serial bus (USB), a micro-USB port, a high definition multimedia (HDMI) port, a video port, an audio port, a Bluetooth™ port, a near-field communication (NFC) port, another like communication interface, or any combination thereof. The system 100 can be powered by a sufficient battery source to remain portable. In another embodiment the system 100 can be powered by a corded connection to an outlet.

Figure 7:
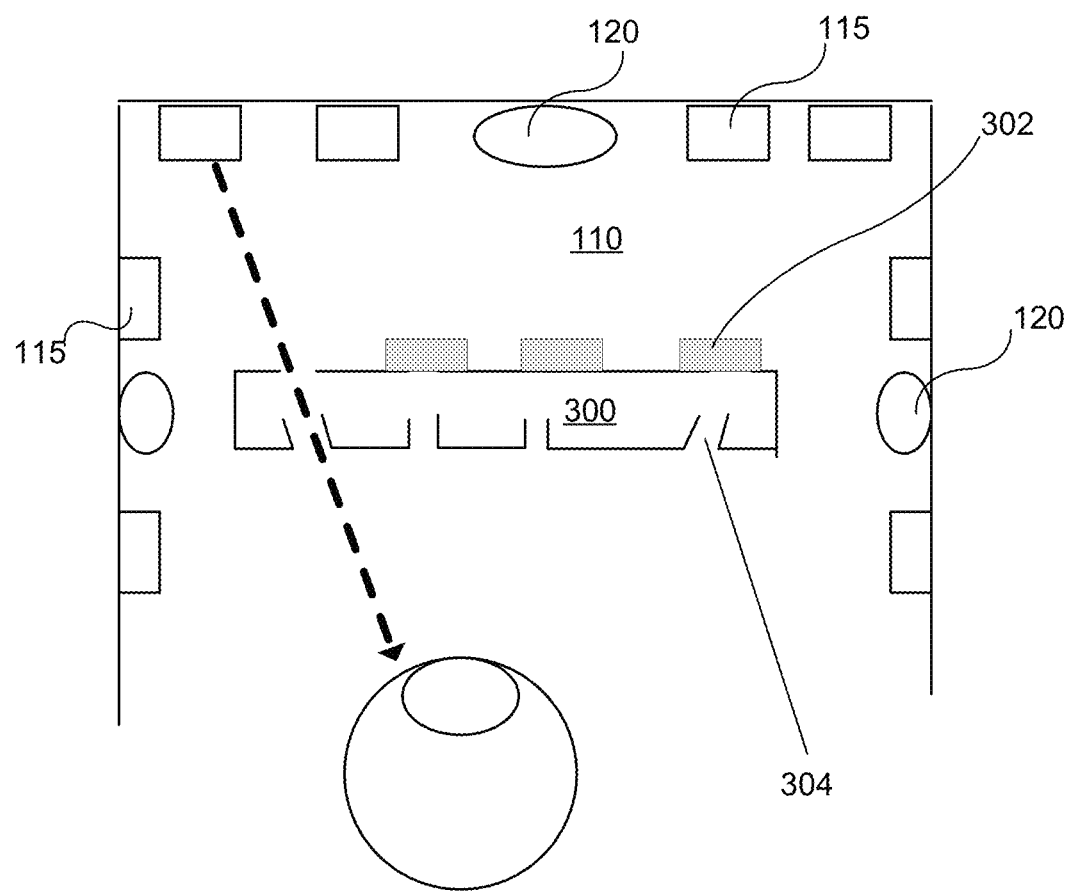
FIG. 7 Depicts a top view of an aperture device in a cavity, in accordance with an exemplary embodiment.

As shown in FIG. 7, the system 100 comprises an aperture device 300. The aperture device 300 can be oriented between the light source 115 and the eye of the patient. The aperture device 300 can be configured to provide a collimated array of light toward the eye for a slit eye test. In another embodiment, the aperture device 300 can be configured to provide an annular arrangement of light toward the eye of the patient for a keratometry analysis. In one aspect, the aperture device 300 can be oriented inside of the cavity 110. The aperture device 300 can comprise a shutter 302 covering an aperture 304 that can be opened or closed.

In a further aspect, the aperture device 300 can comprise a plurality of apertures 304 oriented along a length of the aperture device 300. The plurality of apertures 304 can be used to change the angle of the collimated arrangement of light transferred to the eye of the patient. In another aspect, the aperture device 300 can comprise servo-motors or other types of actuators in communication with the controller 125, such that the controller can define which aperture should be open for a particular portion of the slit eye test. Similarly, a different configuration of the aperture 304 and shutter 302 can be devised to transfer an annular arrangement of light towards the eye in the a keratometry analysis. In a further aspect, the aperture device 300 can be accessed in the cavity 110 through the access panel 160. The aperture device 300 can be inserted and removed from the cavity to allow other tests to be performed. In a further aspect, the aperture device 300 can be coupled to an internal surface of the housing 105 using alignment fixture such as a channel (not shown). Other potential alignment mechanisms are possible.

Figure 8:
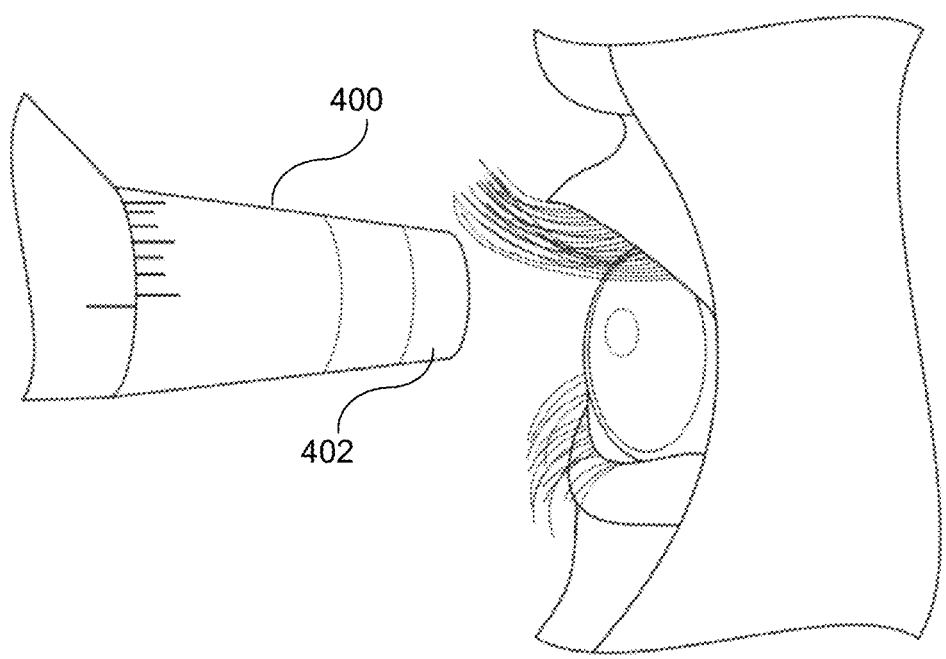
FIG. 8 depicts a sprayer attachment for various tests, in accordance with an exemplary embodiment.

In another embodiment as shown in FIG. 8, the system 100 can further comprise a sprayer 400. The sprayer 400 can be used as a part of the air pressure test. The sprayer 400 can be oriented in the cavity 110. To initiate the test, the sprayer 400 can be coupled to the housing by accessing the cavity 110 through the access panel 160. In an aspect of the embodiment, the sprayer 400 can be in communication with the controller 125 such that in the controller can provide instructions to operate the sprayer. In another aspect, the sprayer 400 can be configured to disperse a plurality of materials towards the eye. For example, the sprayer 400 can be configured to disperse air, particulates, or fluids towards the eye. In a further aspect of the embodiment, the sprayer attachment 400 can be used in a therapeutic manner to provide medication towards the eye. In another embodiment, the sprayer 400 can be coupled to an exterior portion of the housing 105, wherein the sprayer 400 can be oriented to disperse material towards the patient's eye.

Figure 9:
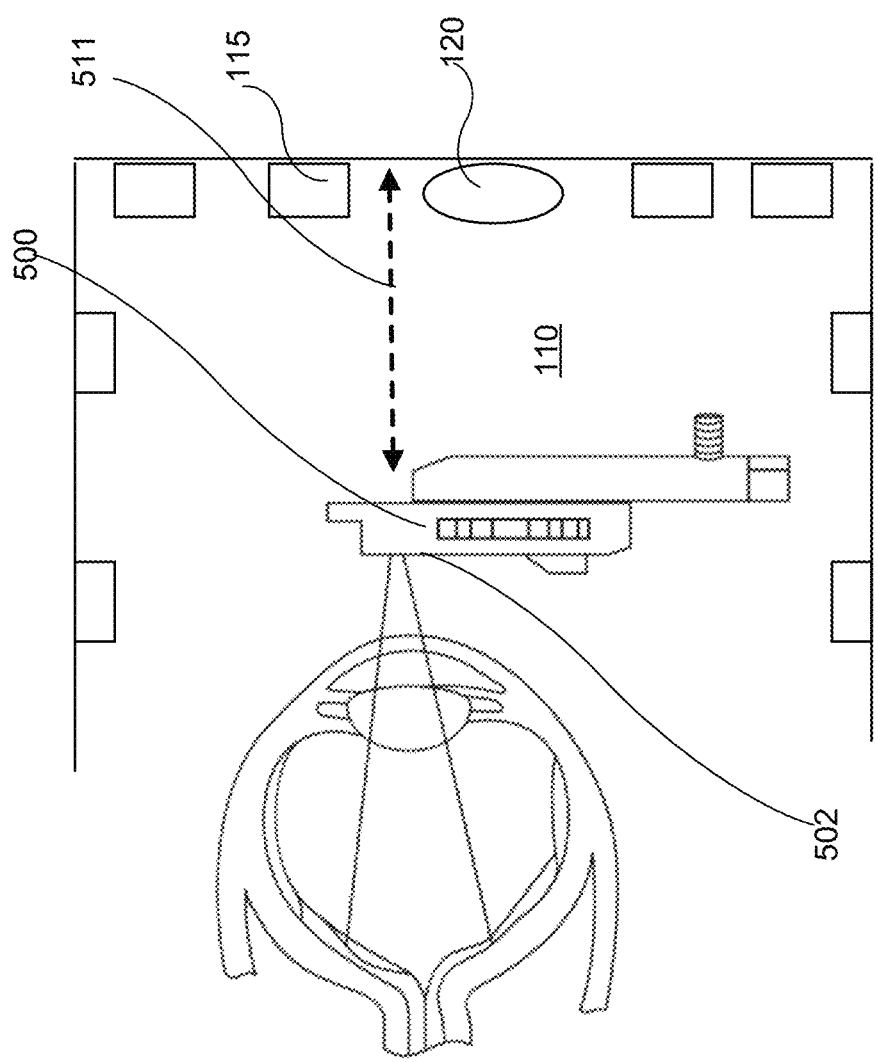
FIG. 9 depicts a side schematic view of a system performing a fundoscopic exam, in accordance with an exemplary embodiment.

In another aspect as shown in FIG. 9, a lens device 500 can be coupled to the housing 105. In one aspect, the lens device 500 can be displaced within the cavity 110. In a further aspect, the internal configuration can orient the lens 502 between an imager 125 and an interior wall of the housing. In an aspect, the lens device 500 can be motorized and in communication with the controller 125. In a further aspect, the lens device 500 can be adjusted by the controller 125 to focus on different interior regions of the eye.

8-Point Eye Exam Using the Monitoring System

In a further aspect of the embodiment, the system can reconfigurable to perform a plurality of eye tests. The system 100 can be reconfigured to receive the attachable components such as, the aperture device 300, sprayer 400 or lens device 500, to perform a respective test. The visual acuity test can be performed. In one aspect, a visual acuity exam chart can be displayed on an embodiment of the light sources 125 configured to display letters and symbols. In a further aspect, the controller 125 in conjunction with the communication module 132 can execute instructions on the light sources to guide the patient to read symbols in the chart via audio and/or text instructions. The patient can respond using the two-way communication components to respond to any prompts from the visual acuity test. In a further aspect, the responses by the patient can be stored within the storage 130 or externally. With a speech processing module in the communication module 132, the controller 125 can automatically record and recognize a patient's response. The response can be converted to a transcript. The system can identify the patient's response as correct if it matches the symbol/letter correctly and incorrect otherwise. Depending on patients' responses, the device can automatically adapt the sequence in the test to change the order of the letter or size fonts. For example, this adaptability feature can start a test with a medium size character and if the patient is not able to recognize the letters, then the test can start displaying a larger font. In another aspect, if the patient is able to recognize medium size letters correctly, then the system 100 can adapt by displaying smaller fonts to efficiently determine the patient's visual acuity. The system 100 can also operate semi-autonomously in which the health care provider or examiner can also see what is displayed to the patient and ask the patient to read items from chart personally and examine the correctness of the patient himself/herself. Moreover, the same examination can be performed as part of a telemedicine application in which doctors can control the system 100 remotely from a different environment than the patient. Further, as a part of a telemedicine protocol, the health care provider can diagnose the patient, communicate the diagnosis to the patient at the remote site and potentially initiate a form of treatment.

Figure 10:
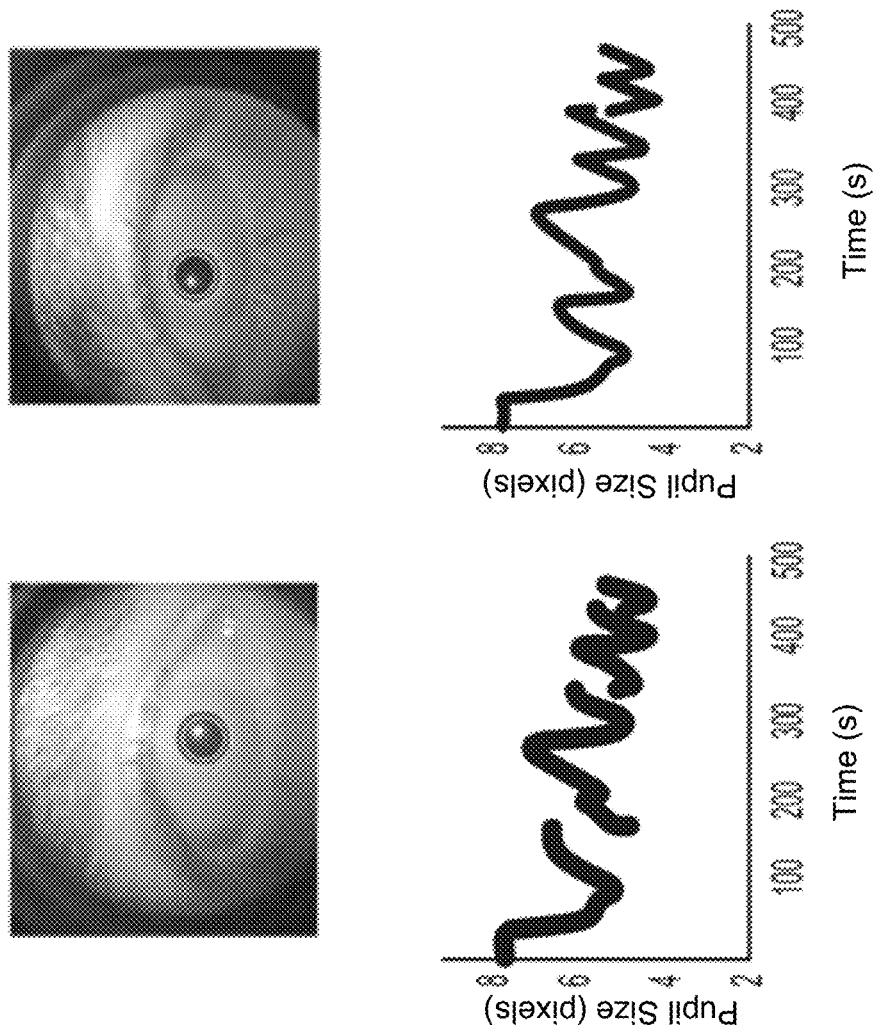
FIG. 10 depicts a sample response performed during pupil dilation test, in accordance with an exemplary embodiment.

In another aspect, pupil response can be evaluated. For example, an array of light sources 115 can be used to stimulate a patient's pupils and their reactions can be recorded by the imagers 125. A visual assessment of the pupils via image processing algorithms can be executed by the controller to detect any observable abnormalities. As shown in FIG. 10, the response of the pupils can be charted, analyzed and stored. Similar to the visual acuity test, telemedicine applications can be used. Other experts can assess the health of the pupil in a remote environment subjectively or quantitatively.

In another aspect, extraocular motility and alignment can be evaluated. The system 100 can prompt the patient to look in the six-cardinal position of gaze. This test can be performed while both eyes are open. Moreover, the test can also be performed on each eye separately while the other eye is kept closed. The system can track the eyes of the user to measure the range of pupil motion. This exam can be performed fully-autonomously, semi-autonomously, and in a telemedicine setup. In addition to the standard examination in which user are instructed to look at six discrete points, the system can perform the extraocular examination with continuous lighting. For example, in the discrete examination, a light stimulus can turn off at a specific location and another light stimulus can turn on at a further location. In the continuous light examination, testing procedure can go from one location to another location by sequentially lighting the stimulus in between.

In another aspect, intraocular pressure can be evaluated. In particular, the system 100 can be used to perform Goldman tonometry. For example, the sprayer 400 can be used to disperse materials towards the eye. For example, the sprayer 400 can disperse anesthetic eye drops followed by fluorescein dye. The system 100 can illuminate the impacted regions of the eye using the light source 115. In a further aspect, the system 100 can illuminate the regions with LEDs and the sprayer 400 can be used to gently press the eye to indent the cornea. The sprayer 400 can further comprise sensors to measure the pressure enforced by the cornea to identify intraocular pressure. In addition to measuring the pressure with the physical sensors 402 on the apparatus, the system 100 can measure the pressure optically with the imaging sensors capturing the indentation procedure. The device can also perform non-contact tonometry with an "air puff" test. The sprayer 400 within the system 100 cavity can puff air to flatten the cornea. The optical sensors can measure the time it takes to flatten the cornea as well as the time it takes for cornea to go back to its normal shape after the flattening. The intraocular pressure can be measured based on the measured time duration.

In another aspect the system 100 can be used to determine confrontational visual fields. During the test, a visual stimulus can be illuminated at different locations to assess the visual field of the patient. The shape and size of the visual stimuli can be adaptive based on the response of the patient. The examination can be executed similar to standard subjective examinations by displaying a hand with varying number of fingers pointing up and asking the number of fingers. Further, other types of stimulus such as different size, shape and number can be displayed on the light source arrangement. Similar to visual acuity test, this procedure can be performed autonomously, semi-autonomously, and in a telemedicine context. In the fully-autonomous mode, the instructions can be provided by the system 100 through the communications module 132. The reaction of the subject can be recorded and processed. If patient's response matches, the system can display more challenging stimulus or vice versa. In the semi-autonomous mode, the examiner can interact with the patient while being in the same environment or in a remote environment.

Figure 11:
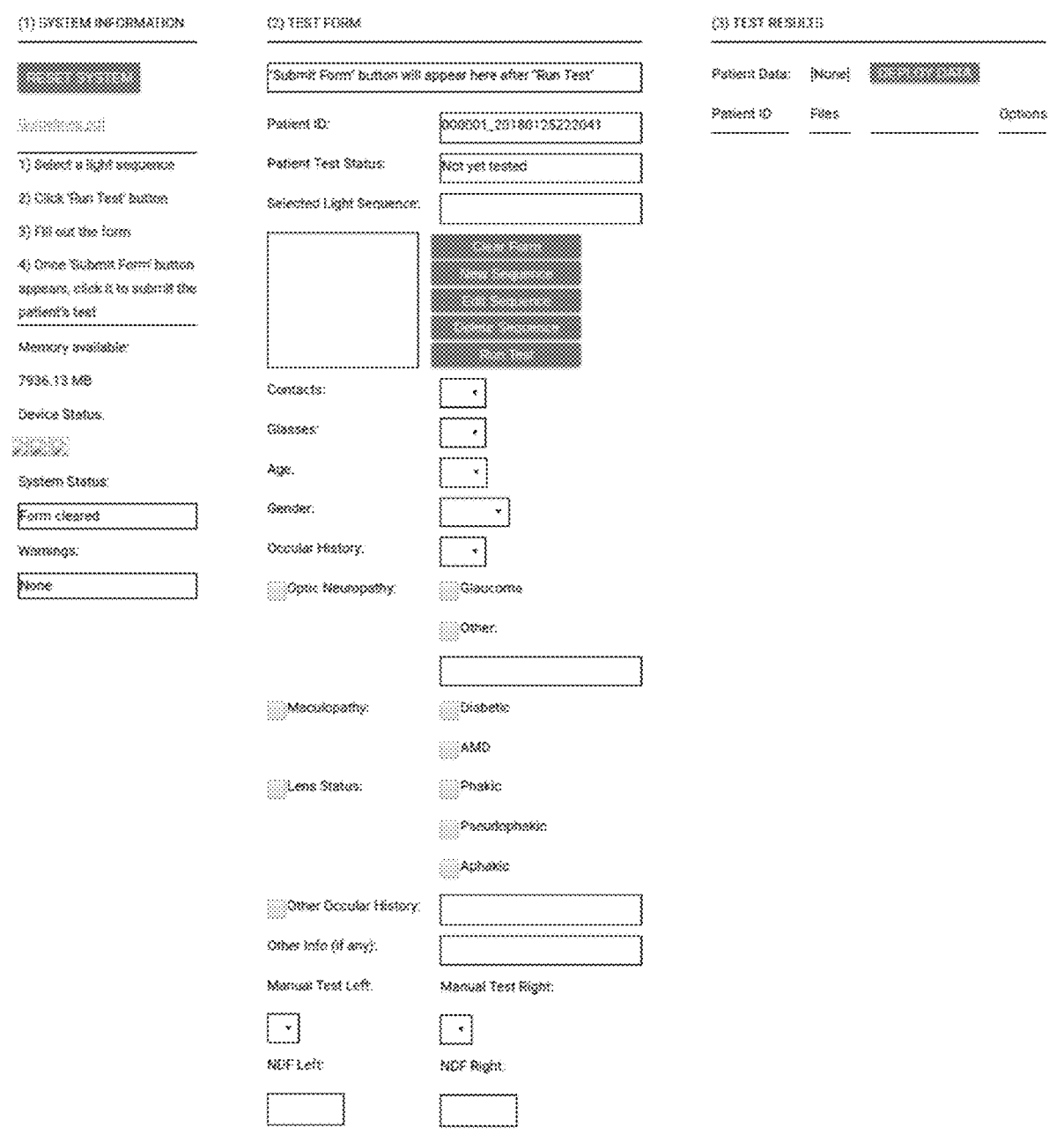

The system can also perform an external examination of the patient's orbital region. The system 100 can execute an external examination in telemedicine context as well as in a fully autonomous manner. In the telemedicine setup, examiner can visually assess the patient's eyes via HD streamed videos in a remote location. Even though the examiner is in a different location, he/she can fully control the lighting and imager configurations within the system 100 and interact with the user via audio and visual domains via the communications module 132. For example, in FIG. 11, the interface with the GUI 140 can be manipulated by an operator or health care provider to provide instructions for executing a particular test. In the fully autonomous mode, the health care provider can automatically assess the external structure eyes with image processing, computer vision, and machine learning algorithms.

Figure 12C:
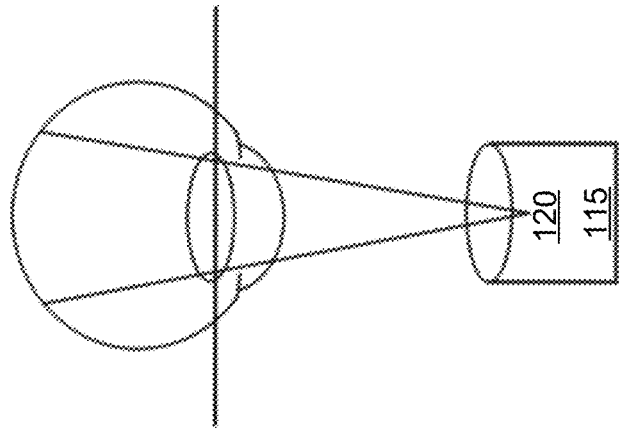
FIGS. 12 A-C depict schematic arrangements of light source illumination for a slit eye test, in accordance with an exemplary embodiment.
Figure 12B:
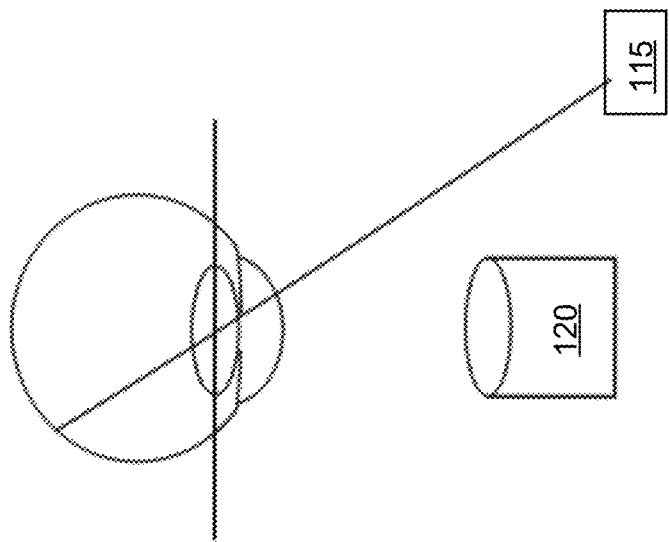
Figure 12A:
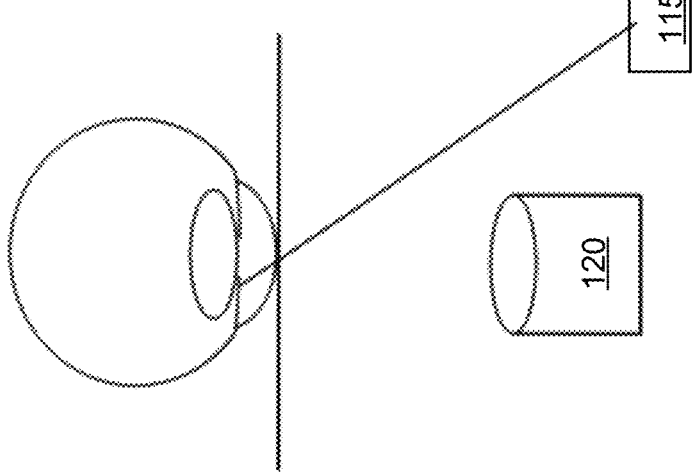

As shown in FIG. 12, the slit-lamp examination can be used. With the aperture device 300, the system 100 can assess the status of lids, lashes, lacrimal system, conjunctiva/sclera, cornea, anterior chamber, iris, lens, and anterior vitreous. Similar to other examination procedures, the slit-lamp examination can be fully autonomously or via telemedicine.

Figure 13:
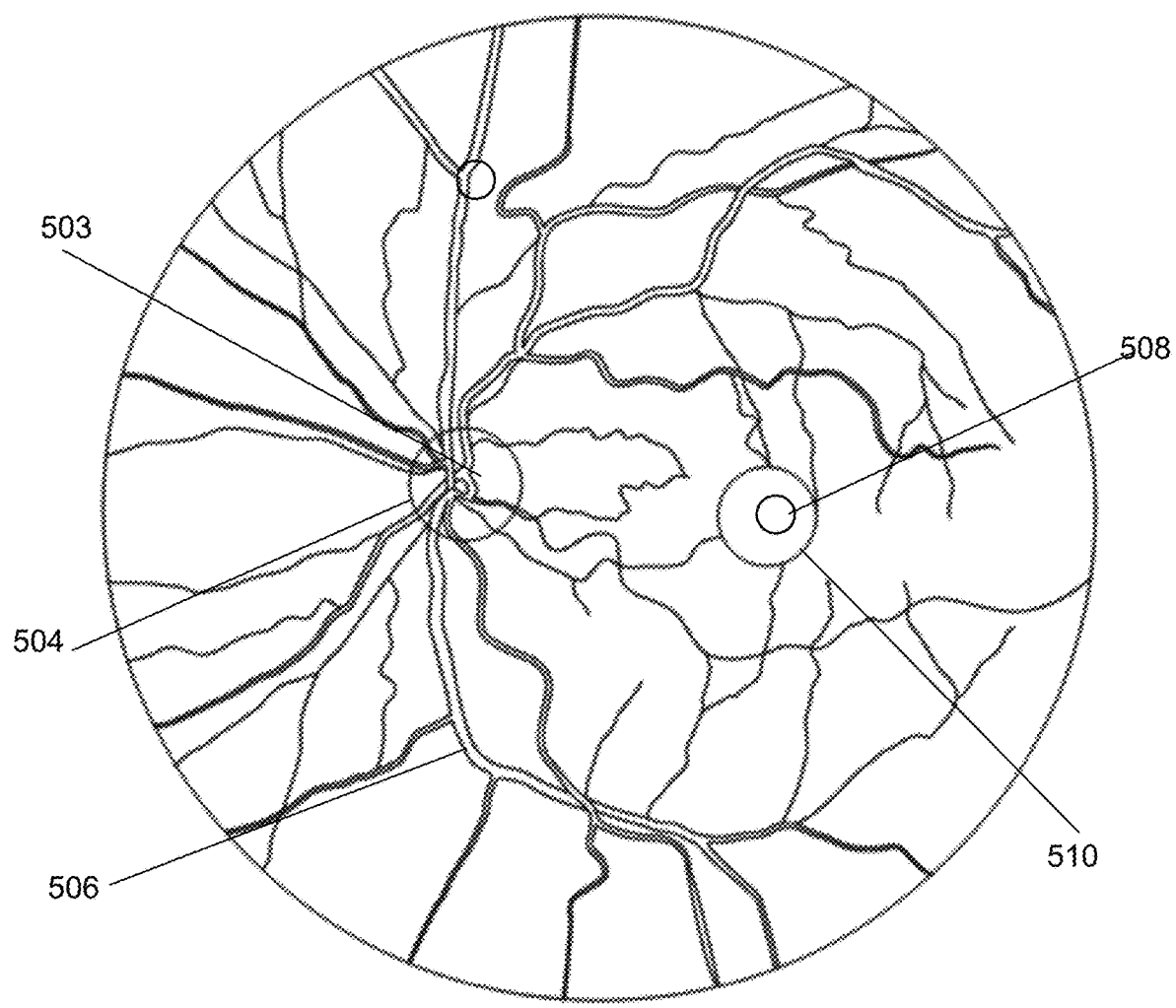
FIG. 13 depicts a front magnified view captured to a lens in a fundoscopic exam, in accordance with an exemplary embodiment.

In another embodiment the system 100 can perform a fundoscopic examination. As shown in FIG. 13, the lens device 500 within the system can enable looking through the pupil and focusing on the retina. In this view, the optic cup 503, optic disc 504, blood vessels 506, fovea 508 and macula 510 can be evaluated. The lens device 500 can further comprise an autofocus mechanism which can adjust the focus of the resultant images automatically before capturing high quality fundus image. The quality of the images can be measured with a no-reference image quality assessment metric developed for fundus images. The system 100 can also optimize the image acquisition configuration by maximizing the objective quality score. The objective quality metric is based on the statistics of the captured image. In one aspect, the auto focusing by the controller 125 can be the result of a statistical analysis derived from the image. The dissimilarity/difference between the statistics of the captured image and an ideal image configuration can determine an objective quality score. Frequency characteristic of the fundus image can be essential to obtain the objective quality score. The autofocusing capabilities attributed to the lens device 500 are not limited to the fundoscopic analysis. The autofocusing capabilities can be similarly applied to the imagers 120 used in other embodiments and for the other types of tests.

In another embodiment, the system 100 can evaluate ocular biometry. During the measurement, the system can measure the axial length, anterior chamber depth, lens thickness, and white-to-white along with a corneal power measurement. These measurements can be used in intraocular lens power calculations for cataract surgery. Length measurements can be obtained with either ultrasound, laser interference, or swept source OCT.

In yet another embodiment the system 100 can execute a keratometry exam. The system 100 can evaluate the shape and refractive power of the cornea. Using the aperture device 300, the system can transfer concentric circles of white rings toward the cornea. The distortion determined can be measured to generate the corneal shape and refractive power.

Figure 14:
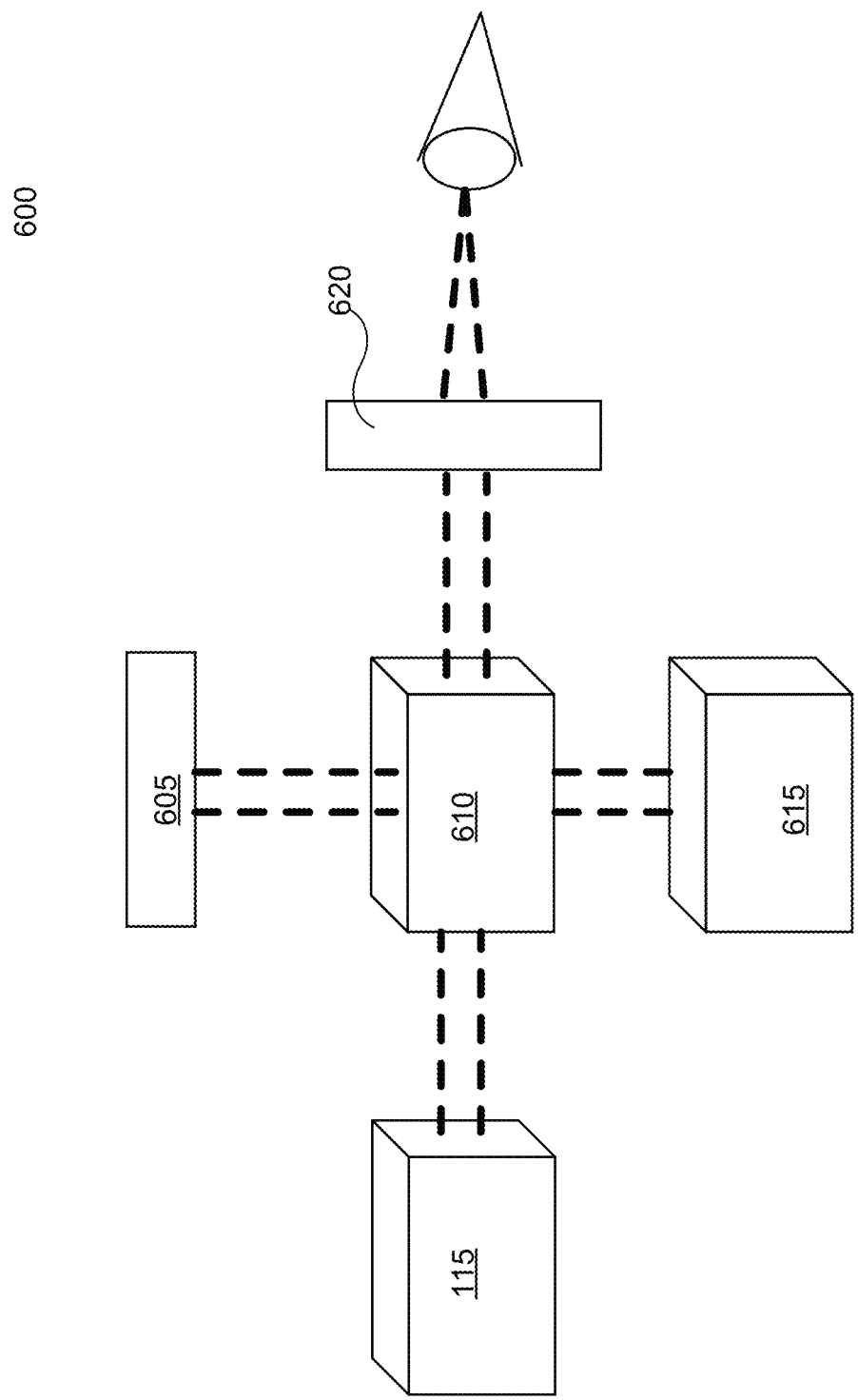
FIG. 14 depicts an OCT integrated into a cavity, in accordance with an exemplary embodiment.

In another embodiment, the system 100 can be configured to execute Optical Coherence tomography (OCT). As shown in FIG. 14, the system 100 can be configured to capture cross-section images of the retina with the imaging setup. In an aspect of the embodiment, an OCT subsystem 600, can comprise the light source 115, a reference mirror 605, a beam splitter 610, a photodetector 615, and an optical lens 620. In a further aspect of the embodiment, the light source can be a low-coherence broad bandwidth light source. In a further aspect, the subsystem components can be integrated into the cavity 110 of the system 100.

Figure 15:
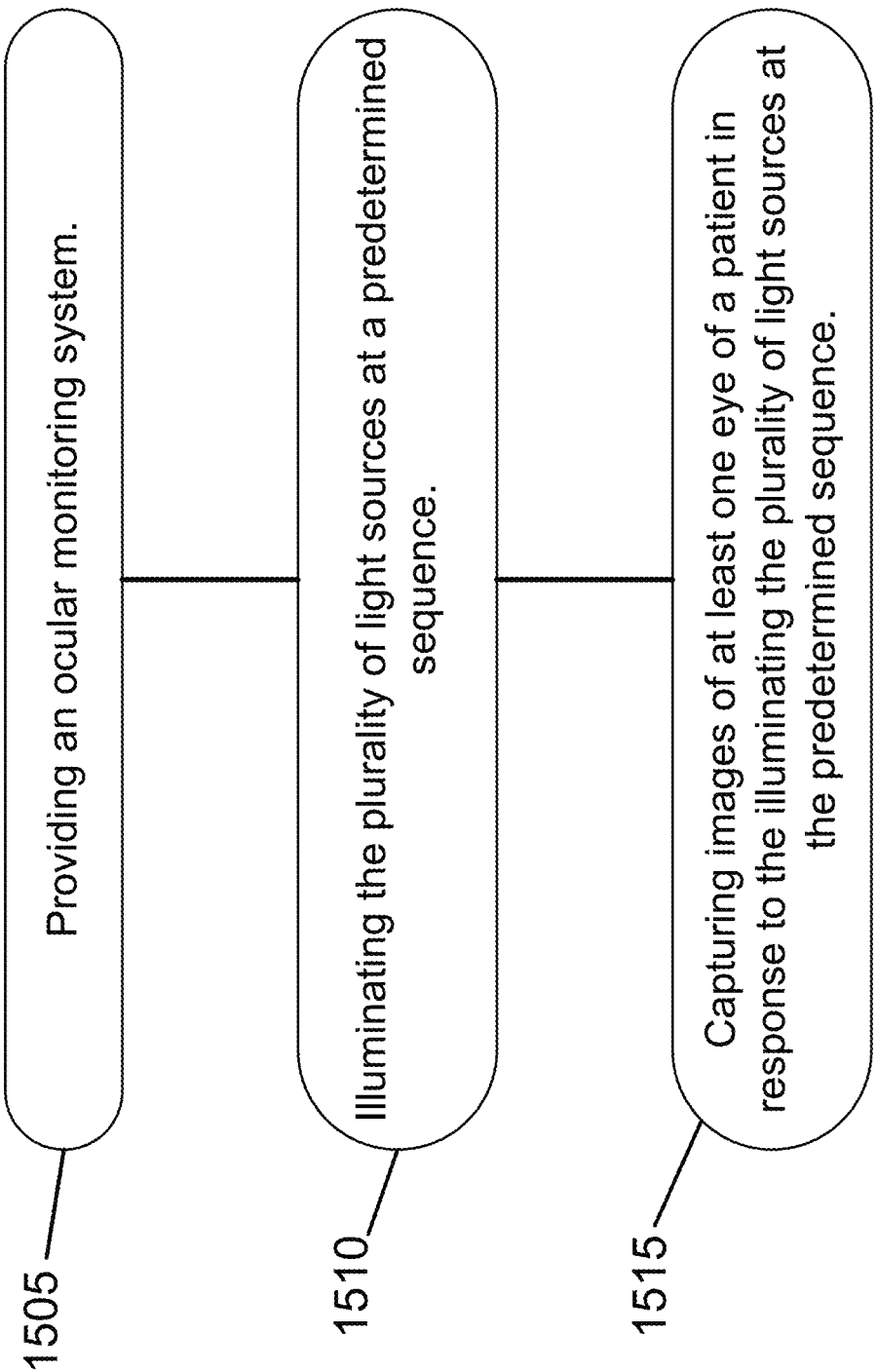
FIG. 15 depicts a block diagram of an example method for monitoring ocular response.

FIG. 15 is a flowchart representing an example method for monitoring ocular movement. The example method 1500 can be implemented by the system 100. The operations described and shown in the method 1500 of FIG. 15 may be carried out or performed in any suitable order as desired in various embodiments of the disclosure. Additionally, in certain embodiments, at least a portion of the operations may be carried out in parallel. Furthermore, in certain embodiments, less than or more than the operations described in FIG. 15 may be performed. The method 1500 can start in block 1505, wherein an ocular monitoring system can be provided. The system can comprise a housing that defines a cavity configured to allow each eye of a patient to view an interior region of the housing. A plurality of light sources can be oriented within the interior region of the housing. At least one imager can be oriented to capture an image of an eye of a patient during an evaluation.

At Block 1510, the method can comprise illuminating the plurality of light sources at a predetermined sequence. In a further aspect, Block 1510 can comprise illuminating a first light source in the plurality of light sources at a first time and illuminating a second light source in the plurality of light sources at a second time different than the first time. In yet a further aspect, Block 1510 can comprise illuminating a third light source in the plurality of light sources at a third time different than the first and second times; and illuminating a fourth light source in the plurality of light sources at a fourth time different than the first, second, and third times.

At Block 1515, the method can comprise capturing images of at least one eye of a patient in response to the illuminating the plurality of light sources at the predetermined sequence. Block 1515 can further comprise capturing a first image of a left eye of a patient during illumination of the first light source; and capturing a second image of a left eye of a patient during illumination of the second light source. In a further aspect, capturing images of at least one eye of a patient comprises capturing a first image of a left eye of a patient during illumination of the first light source; and capturing a second image of a left eye of a patient during illumination of the second light source. In yet a further aspect, capturing images of at least one eye of a patient can comprise capturing a third image of a right eye of a patient during illumination of the third light source; and capturing a fourth image of a right eye of a patient during illumination of the fourth light source.

The method 1500 can further comprise illuminating a first region of an eye of a patient with a collimated beam of light; capturing an image of the first region of the eye of the patient; illuminating a second region of an eye of a patient with the collimated beam of light; and capturing an image of the second region of the eye of the patient. In yet a further aspect, the collimated light source can be oriented in a fixed position within the interior region of the housing.

The method 1500 can further comprise spraying with a sprayer at least one of a fluid, air or particulate towards an eye of a patient. In a further aspect, the method 1500 comprises capturing an image of an eye of the patient in response to the spraying the eye.

The method 1500 can further comprise inserting a lens to a position between the imager an eye of a patient. In a further aspect, the method 1500 can comprise focusing the imager on a portion of an eye of the patient beneath the surface of the eye. In yet a further aspect, the method can comprise capturing an image of the portion of an eye of the patient.

While certain embodiments of the disclosure have been described in connection with what is presently considered to be the most practical and various embodiments, it is to be understood that the disclosure is not to be limited to the disclosed embodiments, but on the contrary, is intended to cover various modifications and equivalent arrangements included within the scope of the appended claims. Although specific terms are employed herein, they are used in a generic and descriptive sense only and not for purposes of limitation.

This written description uses examples to disclose certain embodiments of the disclosure, including the best modes, and also to enable any person skilled in the art to practice certain embodiments of the disclosure, including making and using any devices or systems and performing any incorporated methods. The patentable scope of certain embodiments of the disclosure is defined in the claims, and may include other examples that occur to those skilled in the art. Such other examples are intended to be within the scope of the claims if they have structural elements that do not differ from the literal language of the claims, or if they include equivalent structural elements with insubstantial.

What is claimed is:

1. A system for monitoring ocular movement comprising:
 a housing that defines a first cavity configured to allow a first eye of a patient to view a first interior region of the housing;

at least two light sources oriented within the first interior region of the housing;
a first imager oriented to capture an image of a first eye of a patient during an evaluation; and
a first controller comprising first processor and a first non-transitory computer readable medium storing instructions that, when executed by the first processor, cause the first controller to:
illuminate a first light source of the light sources within the first interior region at a first time;
receive first image data from the first imager indicative of a first image of a first eye of a patient during illumination of the first light source within the first interior region;
illuminate a second light source of the light sources within the first interior region at a second time different than the first time; and
receive second image data from the first imager indicative of a second image of a first eye of a patient during illumination of the second light source within the first interior region.

2. The system of claim 1, wherein the housing further defines a second cavity configured to allow a second eye of a patient to view a second interior region of the housing such that light emanating from the first light source is confined to the first interior region of the housing.

3. The system of claim 1, wherein the light sources comprise light emitting diodes (LEDs).

4. The system of claim 1 further comprising a gimbal system coupled to the first imager;
wherein the gimbal system is configured to adjust a focus region by the first imager upon a first eye of a patient.

5. The system of claim 1 further comprising an aperture device configured to transmit a collimated beam of light towards one or more regions of a first eye of a patient.

6. The system of claim 5, wherein the aperture device is in a fixed position within the first interior region of the housing.

7. The system of claim 1 further comprising a sprayer configured to spray one or more of a particulate, a liquid, or air towards a first eye of a patient.

8. The system of claim 1 further comprising a lens device coupled to the housing;
wherein the lens device is configured to orient a focal region of the lens device onto a section of an interior portion of a first eye of a patient beneath a surface of the first eye.

9. The system of claim 2, wherein the instructions, when executed by the first processor, further cause the first controller to:
illuminate a third light source within the second interior region at a third time different from the first and second times;
receive third image data from the first imager indicative of a third image of a second eye of a patient during illumination of the third light source within the second interior region;
illuminate a fourth light source within the second interior region at a fourth time different than the first, second, and third times; and
receive fourth image data from the first imager indicative of a fourth image of a second eye of a patient during illumination of the fourth light source within the second interior region.

10. A method for monitoring ocular movement comprising:
providing an ocular monitoring system comprising:
a housing that defines a cavity configured to allow each eye of a patient to view an interior region of the housing;
a plurality of light sources oriented within the interior region of the housing; and
an imager oriented to capture an image of an eye of a patient during an evaluation;
illuminating a first light source in the plurality of light sources at a first time;
illuminating a second light source in the plurality of light sources at a second time different than the first time;
capturing a first image of a first eye of a patient during illumination of the first light source; and
capturing a second image of a first eye of a patient during illumination of the second light source.

11. The method of claim 10 further comprising:
illuminating a third light source in the plurality of light sources at a third time different than the first and second times;
illuminating a fourth light source in the plurality of light sources at a fourth time different than the first, second, and third times;
capturing a third image of a second eye of a patient during illumination of the third light source; and
capturing a fourth image of a second eye of a patient during illumination of the fourth light source.

12. The method of claim 10 further comprising:
illuminating a first region of an eye of a patient with a collimated beam of light from a collimated light source of the ocular monitoring system located within the interior region of the housing;
capturing an image of the first region of an eye of the patient;
illuminating a second region of an eye of a patient with the collimated beam of light; and
capturing an image of the second region of an eye of the patient.

13. The method of claim 12, wherein collimated light source is in a fixed position within the interior region of the housing.

14. The method of claim 10, further comprising:
spraying, using a sprayer of the ocular monitoring system, at least one of a fluid, air, or a particulate towards an eye of a patient; and
capturing an image of an eye of the patient in response to the spraying.

15. The method of claim 10 further comprising:
inserting a lens to a position between the imager and an eye of a patient;
focusing the imager on a portion of an eye of the patient beneath the surface of the eye; and
capturing an image of the portion of an eye of the patient.

16. A system for monitoring ocular movement comprising:
a housing defining a cavity;
a first plurality of light sources oriented within a first distinct interior region of the housing;
a first imager oriented within the first distinct interior region and configured to capture an image of a first eye of a user of the system;
a first collimated light source oriented in the first distinct interior region and configured to direct a first collimated beam of light towards a first region of the first eye of the user;
a first focusing lens configured to focus the first imager on an interior region of the first eye of the user beneath a surface of the first eye of the user; and a controller configured to:
- illuminate a first light source in the first plurality of light sources at a first time;
- cause the first imager to capture an image of the first eye of the user during illumination of the first light source;
- illuminate a second light source in the first plurality of light sources at a second time different than the first time;
- cause the first imager to capture an image of the first eye of the user during illumination of the second light source;
- cause the first imager to capture an image of the region of the first eye of the user illuminated by the first collimated light source; and
- capture an image of the interior region of the first eye of the user beneath the surface of the eye of the user.

17. The system of claim 16 further comprising:
a second plurality of light sources oriented within a second distinct interior region of the housing;
a second imager oriented within the second distinct interior region and configured to capture an image of a second eye of a user of the system;
a second collimated light source oriented in the second distinct interior region and configured to direct a second collimated beam of light towards a region of the second eye of the user;
a second focusing lens configured to focus the second imager on an interior region of the second eye of the user beneath a surface of the second eye of the user; and
a controller configured to:
- illuminate a first light source in the second plurality of light sources at a third time different from the first and second times;
- cause the second imager to capture an image of the second eye of the user during illumination of the first light source in the second plurality of light sources;
- illuminate a second light source in the second plurality of light sources at a fourth time different than the first, second, and third times;
- cause the second imager to capture an image of the second eye of the user during illumination of the second light source in the second plurality of light sources;
- cause the second imager to capture an image of the region of the second eye of the user illuminated by the second collimated light source; and
- capture an image of the interior region of the second eye of the user beneath the surface of the second eye of the user.

18. The system of claim 16, wherein the first focusing lens is movable between a storage position and a focusing position.

19. The system of claim 1, wherein the housing further defines a second cavity configured to allow a second eye of a patient to view a second interior region of the housing; and
wherein the system further comprises:
- at least two light sources oriented within the second interior region of the housing;
- a second imager oriented to capture an image of a second eye of a patient during an evaluation; and
- a second controller comprising a second processor and a second non-transitory computer readable medium storing instructions that, when executed by the second processor, cause the second controller to:
  - illuminate a first light source of the light sources within the second interior region at a first time;
  - receive first image data from the second imager indicative of a first image of a second eye of a patient during illumination of the first light source within the second interior region;
  - illuminate a second light source of the light sources within the second interior region at a second time different than the first time; and
  - receive second image data from the second imager indicative of a second image of a second eye of a patient during illumination of the second light source within the second interior region.

20. The system of claim 19, wherein each light source comprises a light emitting diode (LED).

21. The system of claim 20, wherein the LEDs are separated into distinct groups; and
wherein each distinct group of LEDs is separately controllable by one or both of the first processor and the second processor.

* * * * *